United States Patent
Ruellan et al.

(10) Patent No.: US 9,709,536 B2
(45) Date of Patent: Jul. 18, 2017

(54) THERMAL FLOW SENSOR, GAS SENSOR COMPRISING AT LEAST ONE SUCH SENSOR AND PIRANI GAUGE COMPRISING AT LEAST ONE SUCH SENSOR

(71) Applicant: COMMISSARIAT A L'ENERGIE ATOMIQUE ET AUX ENERGIES ALTERNATIVES, Paris (FR)

(72) Inventors: Jeremie Ruellan, Grenoble (FR); Laurent Duraffourg, Voiron (FR); Julien Arcamone, St Martin le Vinoux (FR); Philippe Andreucci, Moirans (FR); Eric Colinet, Grenoble (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 78 days.

(21) Appl. No.: 14/429,676

(22) PCT Filed: Sep. 17, 2013

(86) PCT No.: PCT/EP2013/069239
§ 371 (c)(1),
(2) Date: Mar. 19, 2015

(87) PCT Pub. No.: WO2014/044663
PCT Pub. Date: Mar. 27, 2014

(65) Prior Publication Data
US 2015/0247828 A1 Sep. 3, 2015

(30) Foreign Application Priority Data
Sep. 19, 2012 (FR) .................................. 12 58794

(51) Int. Cl.
*G01N 7/00* (2006.01)
*G01N 30/66* (2006.01)
(Continued)

(52) U.S. Cl.
CPC ............. *G01N 30/66* (2013.01); *G01K 17/00* (2013.01); *G01N 25/18* (2013.01); *G01N 27/18* (2013.01); *G01N 2011/0093* (2013.01)

(58) Field of Classification Search
USPC ..................................... 73/23.35, 23.4, 25.01
See application file for complete search history.

(56) References Cited

U.S. PATENT DOCUMENTS

| 5,379,630 A | 1/1995 | Lacey |
| 5,543,805 A * | 8/1996 | Thaniyavarn ........ H01Q 3/2676 342/368 |

(Continued)

FOREIGN PATENT DOCUMENTS

| CN | 1711465 A | 12/2005 |
| CN | 102313625 A | 1/2012 |

(Continued)

OTHER PUBLICATIONS

International Search Report Issued Oct. 9, 2013 in PCT/EP13/069239 Filed Sep. 17, 2013.
(Continued)

*Primary Examiner* — Lisa Caputo
*Assistant Examiner* — Nasir U Ahmed
(74) *Attorney, Agent, or Firm* — Oblon, McClelland, Maier & Neustadt, L.L.P.

(57) ABSTRACT

A thermal flow sensor comprising at least one first element (2) suspended with respect to a support, said first suspended element (2) being of an electrically conductive material, first means (6) for biasing said suspended element (2) and first means (8) for measuring the variation of the electric voltage at the terminals of the suspended element (2), said first suspended element (2) being formed by a nanowire and said first biasing means (6) are formed by an alternating current (Continued)

source the intensity of which provides heating of the first suspended element (2) by Joule effect.

18 Claims, 6 Drawing Sheets

(51) Int. Cl.
*G01N 27/18* (2006.01)
*G01K 17/00* (2006.01)
*G01N 25/18* (2006.01)
*G01N 11/00* (2006.01)

(56) References Cited

U.S. PATENT DOCUMENTS

| | | | |
|---|---|---|---|
| 6,169,965 B1 | 1/2001 | Kubisiak et al. | |
| 6,598,459 B1* | 7/2003 | Fu | G01N 33/0031 73/23.34 |
| 8,087,151 B2* | 1/2012 | Park | G01N 27/12 29/592.1 |
| 2008/0314148 A1* | 12/2008 | Robert | B81B 3/0086 73/514.33 |
| 2010/0012919 A1 | 1/2010 | Park et al. | |
| 2010/0219489 A1* | 9/2010 | Duraffourg | B81B 3/0086 257/416 |
| 2011/0179852 A1* | 7/2011 | Polonsky | G01N 30/6095 73/23.36 |
| 2012/0024043 A1 | 2/2012 | McBrady et al. | |
| 2012/0272742 A1 | 11/2012 | Andreucci et al. | |
| 2013/0144542 A1 | 6/2013 | Ernst et al. | |
| 2013/0170517 A1 | 7/2013 | Duraffourg et al. | |
| 2013/0214644 A1 | 8/2013 | Hentz et al. | |
| 2014/0026637 A1 | 1/2014 | Blanc et al. | |
| 2014/0076024 A1 | 3/2014 | Duraffourg et al. | |
| 2014/0079091 A1 | 3/2014 | Ruellan et al. | |
| 2014/0148575 A1 | 5/2014 | Forge et al. | |
| 2014/0162392 A1 | 6/2014 | Ollier et al. | |

FOREIGN PATENT DOCUMENTS

| | | |
|---|---|---|
| CN | 102667465 A | 9/2012 |
| EP | 1 840 582 | 10/2007 |
| FR | 2 917 731 | 12/2008 |
| WO | WO 99/34198 A2 | 7/1999 |
| WO | 01 44547 | 6/2001 |
| WO | 2011 154363 | 12/2011 |

OTHER PUBLICATIONS

French Search Report Issued Jan. 10, 2013 in French Patent Application No. 1258794 Filed Sep. 19, 2012.

Li, W. et al., "Single-walled Carbon Nanotue Pirani Vacuum Gauge", Solid-State and Integrated Circuit Technology (ICSICT), 10th IEEE International Conference on, IEEE, ( 3 pages) , XP031835238, 2010.

Kawano, T. et al., "An Electrothermal Carbon Nanotube Gas Sensor", Nano Letters, vol. 7, No. 12, pp. 3686-3690, XP055047103, 2007.

Kubota, M. et al., "Silicon sub-micron-gap deep trench Pirani vacuum gauge for operation at atmospheric pressure", Journal of Micromechanics and Microengineering, vol. 21, No. 4, pp. 1-7, XP020188927, 2011.

Kaanta, B. C. et al., "A monolithically fabricated gas chromatography separation column with an integrated high sensitivity thermal conductivity detector", J. Micromech. Microeng., vol. 20, 055016, pp. 1-6, 2010.

Mile, E. et al., "In-plane nanoelectromechanical resonators based on silicon nanowire piezoresistive detection", Nanotechnology, vol. 21, 165504, pp. 1-7, 2010.

Creemer, J. F. et al., "Microhotplates with TiN heaters", Sensors and Actuators A, vol. 148, pp. 416-421, 2008.

Bargatin, I. et al., "Efficient electrothermal actuation of multiple modes of high-frequency nanoelectromechanical resonators", Applied Physics Letters, vol. 90, 093116, (3 pages), 2007.

Razavi, B., "A Study of Phase Noise in CMOS Oscillators", IEEE Journal of Solid-State Circuits, vol. 31, No. 3, pp. 331-343, 1996.

Creemer, J. F. et al., "MEMS Hotplates with TiN as Heater Material", IEEE, vol. 148, pp. 330-333, 2005.

Combined Office Action and Search Report issued Aug. 1, 2016 in Chinese Patent Application No. 201380060312.5 (with English translation).

Detian LI, et al., "The Development of Vacuum Measurement in China", Vacuum and Low Temperature, vol. 10, No. 1, 2004 (submitting English Abstract only).

Jiaqi Wang, "Study on Integrated Pirani Vacuum Sensor System", Database of Chinese Doctoral Dissertations regarding Information, Science and Technology, No. 10, 2010 (submitting English Abstract only).

U.S. Appl. No. 14/519,390, filed Oct. 21, 2014.

U.S. Appl. No. 14/619,656, filed Feb. 11, 2015, Ruellan et al.

Notice of Allowance mailed Apr. 14, 2017, in Chinese Patent Application No. 201380060312.5 (with English-language translation).

\* cited by examiner

THERMAL FLOW SENSOR, GAS SENSOR COMPRISING AT LEAST ONE SUCH SENSOR AND PIRANI GAUGE COMPRISING AT LEAST ONE SUCH SENSOR

TECHNICAL FIELD AND PRIOR ART

The present invention relates to a thermal flow sensor, which can be intended to measure the concentration of a gas or TCD sensor or to measure very low pressures thus forming a Pirani gauge.

Generally, by thermal flow sensor, it is meant any sensor measuring a heat exchange between the sensor body (membrane) and the fluid medium in which the sensor is disposed.

A thermal flow sensor is placed in an environment containing the element to be analysed, an analyte in a carrier gas in the case of a gas sensor or simply a number of gas molecules in the case of a Pirani gauge.

Document WO2001/044547 describes a TCD ("Thermal Conductivity Detectors") sensor using the variation in the thermal conductivity to determine the composition of the gas environment in which it is disposed. It is disposed at the output of a chromatography column. This TCD sensor comprises an elongate support plate, a heating element located on the support plate. The voltage variation is measured at the terminals of the heated support plate to determine the electrical resistance variation which depends on the temperature of the support plate and which is representative of the heat exchanges between the support plate and the gas environment; these heat exchanges depend on the composition of the gas environment. Such a sensor is of a complex manufacture because it requires making the support plate and then making the heating element.

A Pirani gauge is made of a micrometer size suspended filament, it is placed in an enclosure the pressure of which is desired to be measured and it is heated. The pressure measurement is deduced from the quantity of heat lost by the filament as a result of the gas conduction: the molecules that meet the filament absorb part of its energy.

These sensors have the drawback not to allow to get completely rid of the phenomena occurring outside the sensor itself, for example temperature drifts.

Further, generally, it is attempted to reduce the size of the sensors to facilitate the integration thereof and increase the number of fields of application. However, such a downsizing causes an increase in the Flicker noise, also referred to as "1/f Noise".

DISCLOSURE OF THE INVENTION

Consequently, one purpose of the present invention is to provide a thermal flow sensor enabling to avoid at least part of the phenomena occurring outside the reduced size sensor.

It is also a purpose of the present invention to provide a thermal flow sensor of a simpler production than sensors of the state of the art.

The previously set out purpose is achieved by a thermal flow measuring device comprising at least one suspended nanowire intended to be disposed in the environment to be analysed, means for dynamically heating said nanowire and means for measuring the dynamic variation of the electric voltage of the nanowire.

By "dynamic heating", it is intended the application of an alternating electric current of a given period and by "dynamic variation of the electric voltage", the voltage variation due to the electrical resistance variation of the nanowire which results from the time variation in the nanowire temperature.

The implementation of one or more nanowires allows to have sensitive elements having a relatively low thermal time constant, which allows to have a temperature variation of the device which follows the current variation and thus to be able to apply a dynamic excitation signal.

The application of dynamic excitation signals enables the sensor to be made insensitive to slow drifts, for example the temperature drifts of the medium.

The measuring device according to the invention has a high resolution of the measurement of the system temperature.

Further, by virtue of the invention, the excitation signal can have a frequency sufficient to reduce the Flicker noise.

In one particularly advantageous embodiment, the measuring device comprises at least two nanowires or suspended elements.

In one embodiment, means for dynamically heating said nanowire and means for measuring the dynamic variation of the electric voltage of the nanowire are provided.

In another embodiment, one of the nanowires is used for heating by Joule effect, and the other is used for measuring. The "excitation" and "detection" parts are then decoupled allowing a lesser sensitivity relative to the drift of the external parameters, such as temperature.

By multiplying the number of nanowires, the sensor disposed in a channel in which a gas flows can enable heat transfers in the channel to be characterized.

This invention further enables high performance detectors having very small sizes which are co-integratable with microelectronic technologies and CMOS (VLSI)-compatible to be made.

Such a sensor is particularly interesting as a gas sensor used within and/or at the output of a gas chromatography micro-column.

Thus, the subject-matter of the present invention is a thermal flow sensor comprising at least one first element suspended with respect to a support, said first suspended element being of an electrically conductive material, first means for biasing said suspended element and first means for measuring the electric voltage variation at the terminals of the suspended element, said first suspended element being formed by at least one nanowire and said first biasing means being formed by an alternating current source the intensity of which provides heating of the first suspended element by Joule effect. The first suspended element both provides thermal excitation and detection of the resistance variation induced by the alternating heating.

In an exemplary embodiment, the sensor comprises a second suspended element, formed by at least one nanowire, substantially parallel to the first suspended element and away from the first suspended element by a given distance, second means for biasing said second suspended element and second means for measuring the electric voltage variation at the terminals of the second suspended element, the second biasing means being formed by an alternating current source at a frequency different from that of the first biasing means or by a direct current source. The second suspended element thus only provides detection of the resistance variation induced by the alternating heating of the first suspended element.

In another exemplary embodiment, the sensor comprises n first suspended elements substantially disposed parallel to each other, n being a positive integer strictly higher than 1, each first suspended element comprising first means for biasing said first suspended element and first means for measuring the variation of the electric voltage at the terminals of the first suspended element, said first biasing means of the n first elements being formed by an alternating current source having the same frequency or a different frequency the intensity of which provides heating of the corresponding first suspended element by Joule effect respectively. The n suspended elements of the first type provide both thermal excitation and detection of the resistance variation induced by the alternating heating.

In another exemplary embodiment, the sensor comprises m second suspended elements, substantially in parallel to each other, m being a positive integer strictly higher than 1, each second suspended element comprising second means for biasing said second suspended element and second means for measuring the electric voltage variation at the terminals of the second suspended element, the second biasing means being formed by an alternating current source at a frequency different from that of the first biasing means or by a direct current source. The integers n and m can be equal or different depending on the embodiments.

Advantageously, the first biasing means of the n first suspended elements, respectively the second biasing means for biasing the m second suspended elements are common.

For example, the first suspended element can be surrounded between m second suspended elements and/or the second suspended element can be surrounded between n first suspended elements.

In an exemplary embodiment, the n first suspended elements and m second suspended elements are distributed in one or several parallel planes, in the latter case the sensor then extends in three dimensions. This sensor type can enable heat exchanges to be characterized in a fluid channel.

In another exemplary embodiment in which the sensor comprises a first suspended element, the latter can advantageously comprise at least two thermal masses linked to the support, the thermal masses being disposed on either side of the first suspended element. In the case where the sensor comprises n first suspended elements, the sensor can advantageously comprise n+1 thermal masses, said n+1 thermal masses being disposed such that each first element is surrounded by two masses. The masses forming thermostated masses improve heat exchanges.

Advantageously, the first or second suspended element(s) have respectively a width between 10 nm and 1 µm, a length between 1 nm and 100 µm, a thickness between 10 nm and 1 µm, the distance separating the first suspended elements from the second suspended elements is between 10 nm and 10 µm.

For example, a thermal flow sensor according to the invention comprising a first suspended element surrounded with m second suspended elements can be intended to be disposed in a channel. Said suspended elements can then be disposed parallel to the axis of the channel so as to determine the transverse heat exchanges in the gas inside the channel.

Another subject-matter of the present invention is a system for determining the concentration of a gas environment comprising at least one thermal flow sensor according to the invention, an electronics for processing the electric voltage values delivered by the thermal flow sensor.

It is also a subject-matter of the invention to provide a system for determining the pressure in a gas environment comprising at least one thermal flow sensor according to the invention, an electronics for processing the electric voltage values delivered by the thermal flow sensor.

Another subject-matter of the present invention is a device for analysing a gas or gas mixture comprising a gas phase chromatography column and at least one system for determining the concentration according to the invention, said determining system being disposed in a channel connected to the output of the gas chromatography column.

BRIEF DESCRIPTION OF THE DRAWINGS

The present invention will be better understood using the description that follows and the appended drawings wherein.

DETAILED DISCLOSURE OF PARTICULAR EMBODIMENTS

Figures 1, 2:
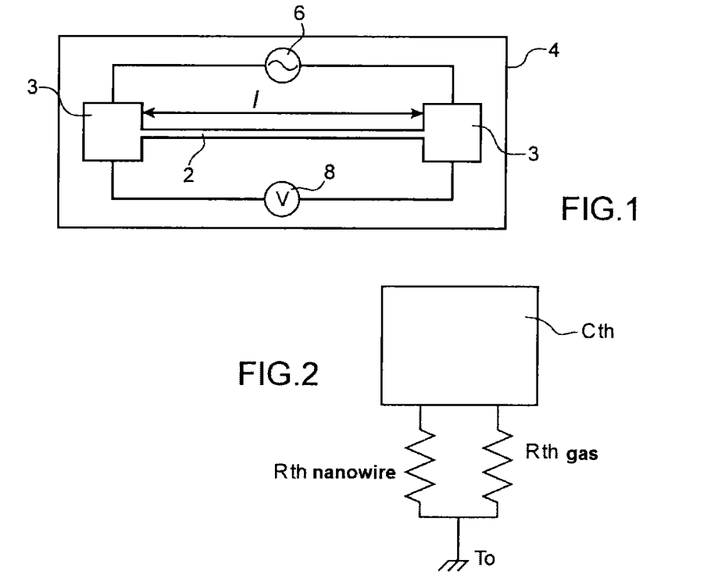
FIG. 1 is a schematic representation of an exemplary sensor with a nanowire.
FIG. 2 is a representation of the thermal model of the sensor of FIG. 1.

In FIG. 1, an exemplary measuring device according to the invention can be seen, comprising a suspended element 2 with respect to a support 4 at its two longitudinal ends. The nanowire 2 is anchored to the support by anchoring pads 3 forming contact pads. The suspended element 2 is a nanowire.

In the description that follows, use is made of the phrase "the terminals of the nanowire"; these are contact pads of the nanowire on the support which are generally formed on the anchoring pads of the nanowire on the support.

The element 2 is of an electrically conductive material, for example of a doped or undoped semi-conductor material, for example of N or P doped silicon, TiN, metal or metal alloys or even silicides, for example of NiSi.

The length of the nanowire is advantageously between 1 µm and 100 µm and the width and thickness of the nanowire are advantageously between 10 nm and 1 µm.

The measuring device also comprises dynamic or modulated excitation means formed by an alternating current source 6 linked to the nanowire 2 and means for detecting the variation amplitude of the voltage at the terminals of the nanowire, formed by a voltmeter 8.

The alternating current source 6 forms means for dynamically heating the nanowire by Joule effect. By virtue of its very small dimensions, the suspended element 2 has a very low thermal inertia and thus a very quick thermal response, which enables a modulated excitation signal to be applied.

The operation of the measuring device of FIG. 1 will now be explained.

The suspended nanowire 2 is disposed in a gas mixture to be analysed.

The nanowire 2 is heated by flowing an alternating current therethrough. By Joule effect, this generates thermal power causing it to be self-heated. The temperature rise of the nanowire depends on heat transfers from the nanowire to the gas environment and to the anchorings. The transfers with the environment mainly control the nanowire heating.

In FIG. 2, the thermal model of the measuring device can be seen.

The heated nanowire can be assimilated to a heat capacity $C_{th}$ connected to a thermostat at a temperature $T_0$ via a heat resistance $R_{th}$ which is assimilated to the resistance of the nanowire $R_{th\ nanowire}$ and the resistance of the gas environment $R_{th\ gas}$.

The principle of the measurement is as follows:

When the analyte concentration in the gas environment is changed, its thermal conductivity is changed. As a result, the heat exchanges between the nanowire and gas environment are changed, and then the temperature of the system varies.

In order to determine this temperature, the electrical resistance of the nanowire which depends on the temperature is determined. The heat resistance is determined by measuring the voltage at the terminals of the nanowire 2 by the voltmeter.

By determining the local temperature of the nanowire, it is possible to deduce the analyte concentration(s) in the carrier gas.

This nanowire which provides its heating and is used for the detection is referred to as nanowire or element of a first type.

The Joule effect power produced by the nanowire is equal to:

$$P_J = R_0 I^2$$

$R_0$ is the initial electrical resistance of the nanowire.

The current source 6 biases the nanowire with an alternating current $I = I_0 \cos(\omega t)$ of an angular frequency $\omega$, as a result there is a power generation at the angular frequency $2\omega$:

$$P_J = \frac{R_0 I_0^2}{2}[1 + \cos(2\omega t)].$$

By virtue of the invention, since the heating element is formed of a nanowire, it has a thermal time constant which is low in comparison to the reciprocal of the thermal excitation frequency, as a result, there is a temperature variation in the nanowire at the same angular frequency:

$$\Delta T = \Delta T_0 (1 + \cos(2\omega t)) \quad (I)$$

The voltage at the terminals of the nanowire then comprises a harmonic at $3\omega$ depending on the temperature.

$$V_{sin\omega} = RI = R_0(1 + TCR \cdot \Delta T_0(1 + \cos(2\omega t)))I_0 \cos(\omega t)$$

$$V_{2\omega} = \frac{1}{2} R_0 I_0 TCR \cdot \Delta T_0 \cos(3\omega t)$$

By filtering and synchronous detection, the temperature of the nanowire can be determined by measuring the amplitude of this harmonic.

The measurement applying a dynamic excitation signal enables to substantially avoid external constant phenomena, such as a slow drift in the environment temperature, which in a sensor of the state of the art can disturb measurements. Besides, the detection at a frequency different from the excitation frequency enables the background signal to be reduced, the major part of the signal measured then depends on the temperature variations due to the Joule effect.

Besides, by virtue of the invention, it is possible to reduce the Flicker noise by applying an excitation signal at a sufficiently high frequency, for example between 10 Hz and 1 MHz and advantageously 1 KHz and 10 KHz.

In the previous calculation, a temperature rise substantially identical throughout the nanowire has been hypothesized. But, in practice, the temperature rise in the nanowire has a parabolic profile.

To take this parabolic profile into account, the resistance variation throughout the length of the nanowire is integrated by taking the temperature profile in the nanowire into account. This hypothesis does not modify the detection principle of the device according to the invention.

Advantageously, a heterodyne measurement can be carried out. For this, a second current $I_{bias}$ at the angular frequency $2\omega - \Delta\omega$ is injected into the nanowire in addition to the excitation signal. The output signal is thus written as:

$$V_{sin\ w} = RI = R_0(1 + TCR \cdot \Delta T_0(1 + \cos(2\omega t)))[I_0 \cos(\omega t) + I_{bias} \cos((2\omega - \Delta\omega)t)]$$

The multiplication of the signals causes the creation of a component of the signal at $\Delta\omega$.

$$V_{\Delta\omega} = \frac{1}{2} R_0 I_{bias} TCR \cdot \Delta T_0 \cos(\Delta\omega t)$$

This method allows on the one hand to detect a signal at a frequency different from the excitation frequency and on the other hand to avoid the electrical cut-off frequency of the system by bringing the detection signal back to a low frequency. A non-attenuated detection signal is thus obtained.

The application of this method is particularly interesting in a high frequency operation.

The application of a bias signal results in causing an undesired heating, but since this is at a different frequency, it does not disturb measurements.

Figure 3:
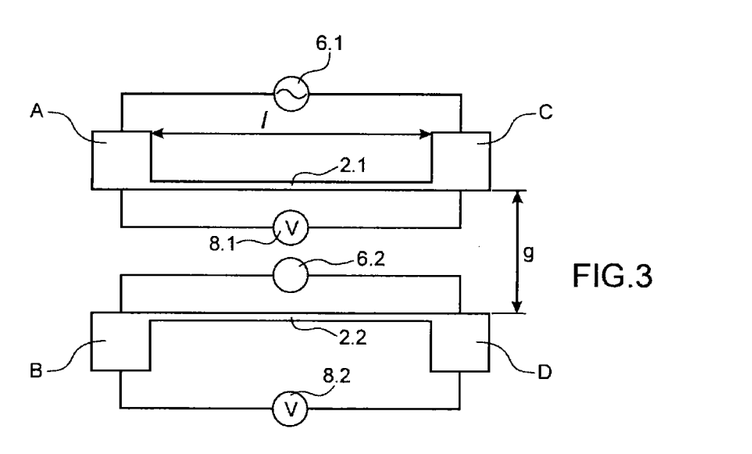
FIG. 3 is a schematic representation of an exemplary sensor with two nanowires.

In FIG. 3, another exemplary thermal flow measuring device implementing two suspended nanowires 2.1, 2.2 disposed substantially parallel to each other and side by side can be seen.

Both nanowires 2.1, 2.2 are suspended to a support 4.

The anchoring points of each nanowire 2.1, 2.2 are respectively referred to as A and C, B and D.

The distance separating both nanowires is preferably lower than 10 µm and higher than 50 nm.

In the case of a Pirani sensor, the value of the distance between the nanowires influences the pressure range in which the sensor is sensitive. The nanowire 2.1 is linked to a first alternating current source 6.1 and to a first means for measuring the voltage 8.1 and the nanowire 2.2 is connected to a second alternating current source 6.2 and to a second means for measuring the voltage 8.2.

The nanowire 2.1 provides thermal excitation of the device and the nanowire 2.2 provides detection. The gas environment to be analysed is located between both nanowires. The nanowire 2.1 is a nanowire of the first type, and the nanowire 2.2 will be referred to as "nanowire of a second type" because it is only used for detection.

The implementation of at least one excitation nanowire and at least one detection nanowire distinct from the excitation nanowire enables the quantity of heat transferred from a suspended element to the other suspended element to be deduced. Further, this implementation allows to avoid the influence of the anchoring of the nanowires on the support. The heat dissipation effect at the anchorings equally acts on both nanowires and a temperature difference is measured between both nanowires.

In the following, the index "in" refers to a physical characteristic of the nanowire 2.1 and the index "out" refers to a physical characteristic of the nanowire 2.2.

The principle of the measurement is the following one:
the system is based on a simultaneous measurement of the temperature in two nanowires facing each other.

Figure 4:
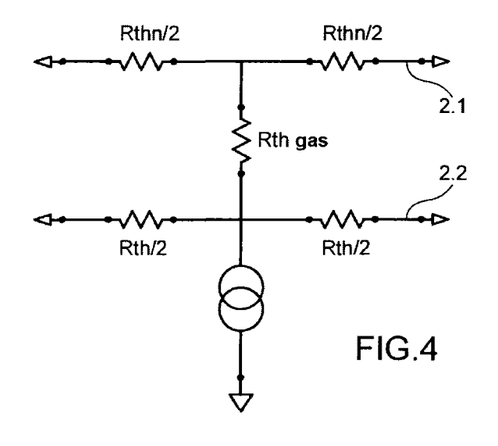
FIG. 4 is a representation of the equivalent circuit diagram of the sensor of FIG. 3.

In FIG. 4, an equivalent circuit diagram of the device can be seen:
the gas environment is represented in the form of a heat resistance linking both nanowires, this resistance being a function of:
  the geometry of the measuring device (heat exchange area, distance between the nanowires),
  the parameters of the gas environment, such as concentration, thermal conductivity, pressure, temperature . . .

$R_{th_n}$ is the heat resistance of a nanowire. In the example considered, both nanowires have an identical resistance.

The nanowire 2.1 is current biased, thereby it generates a thermal power by Joule effect.

Coming back to the operation of the sensor of FIG. 1, the temperature of the nanowire 2.1 is $\Delta T_{in} = \Delta T_{in_0}(1+\cos(2\omega t))$.

This dynamic temperature rise induces a dynamic variation in the electrical resistance of the nanowire 2.1 and thereby in the voltage at its terminals which is written as:

$$V_{in_{3\omega}} = R_{in_0} I_{in_0} TCR \cdot \Delta T_{in_0} \cos(3\omega t) \tag{II}$$

Heat generation in the nanowire 2.1 causes a transfer of this produced heat to the nanowire 2.2 facing thereto via the gas environment located between both nanowires 2.1, 2.2.

In this explanation, only the heat conduction is taken into account, the convection and radiative heat exchange phenomena being neglected.

The thermal resistance value of the gas can be written as:

$$T_{th_{gaz}} = \frac{1}{k_{gaz}} \gamma$$

$\gamma$ is a term in $m^{-1}$ depending in particular on the dimensions of the gas "resistance" and the medium pressure.

Since the temperature in the nanowire 2.1 varies at the angular frequency $2\omega$, the temperature of the nanowire 2.2 varies at the angular frequency $2\omega$.

The temperature variation in the nanowire 2.2 is written as:

$$\Delta T_{out} = \Delta T_{in} \frac{R_{th_n}}{R_{th_n} + R_{th_{gaz}}} \tag{III}$$

With $R_{th_n}$ being the heat resistance due to the nanowires.

The material and the dimensions of the nanowires are selected such that $R_{th_n} \ll R_{th_{gaz}}$, the temperature variation in the nanowire 2.2 can be written from the relationship (III):

$$\Delta T_{out} \cong \Delta T_{in} \frac{R_{th_n}}{R_{th_{gaz}}} \tag{IV}$$

The temperature variation in the nanowire 2.2 is on the other hand proportional to the thermal conductivity variation of the gas.

The nanowire 2.2 exhibits an electrical resistance variation at the angular frequency $2\omega$ which depends on the temperature; it is written as:

$$\Delta R_{out} = TCR \cdot R_{out} \Delta T_{out_e}[1+\cos(2\omega t)] \tag{V}$$

The nanowire 2.2 is also biased to enable the amplitude of the electrical voltage variation at its terminals to be measured. Advantageously, the bias current of the nanowire 2.2 is a direct current. On the one hand, this enables any crosstalking phenomenon to be avoided between the excitation signal and the detection one, since the generated signals vary at different frequencies (3f for the signal of the nanowire in, 2f for the signal of the nanowire out), this enables the detection to be simplified. The voltage variation at the terminals of the nanowire 2.2 also has an angular frequency $2\omega$, wherein this variation at the angular frequency $2\omega$ informs about temperature, and is written as:

$$V_{out} = (R_{out} + \Delta R_{out}) I_{out_e} \tag{VI}$$

The part of the voltage variation at the terminals of the nanowire 2.2 at the angular frequency $2\omega$ ($\Delta R_{out}) I_{out_e}$ is equal to: by coming back to the relationship (V), $$V_{out_{2\omega}} = I_{out_e} TCR \cdot R_{out} \Delta T_{out_e} \cos(2\omega t) \tag{VII}$$

Thus, from the relationships (II) and (VII):

$$\frac{|V_{out_{2\omega}}|}{|V_{in_{3\omega}}|} = \frac{R_{out} I_{out_e} \Delta T_{out_e}}{R_{in} I_{in_e} \Delta T_{in_e}} \tag{VIII}$$

and since $$\Delta T_{out} \cong \Delta T_{in} \frac{R_{th_n}}{R_{th_{gaz}}}, \tag{IV}$$

by setting $$K = \frac{R_{out} I_{out_e}}{R_{in} I_{in_e}},$$

it is obtained from the relationship (VIII), and can be written:

$$\frac{|V_{out_{2\omega}}|}{|V_{in_{3\omega}}|} = K \frac{R_{th_n}}{R_{th_{gaz}}}$$

$$R_{th_{gaz}} = K R_{th_n} \frac{|V_{in_{3\omega}}|}{|V_{out_{2\omega}}|}$$

This conductivity measurement mode enables the influence of the drifts on the material resistivity which would be due to the environment to be removed. These variations are compensated for when the following ratio is measured $$\frac{|V_{out_{2\omega}}|}{|V_{in_{3\omega}}|} = K \frac{R_{th_n}}{R_{th_{gaz}}}$$

By measuring the voltages at the terminals of the nanowires 2.1 and 2.2, the variation in the gas heat resistance between both nanowires can be deduced, the thermal conductivity of the gas environment can be determined and thus its concentration or pressure can be deduced. This determination is independent of the variations in the external environment, such as the temperature variations.

As for the measuring device with one nanowire, a heterodyne measurement can be advantageously carried out by injecting, in the detecting nanowire 2.2, a current at the angular frequency $2\omega - \Delta\omega$. Thus, the electrical signal generated in the detection nanowire 2.2 has a component at $\Delta\omega$ dependent on the temperature.

The thermal flow sensor with one or more nanowires in dynamic operation can be used to make a TCD sensor for measuring gas concentrations or to make a Pirani gauge for measuring a pressure. The pressure range in which the sensor has a high performance depends on the value of the distance separating the nanowires. For example, for a 120 nm distance, the sensor is sensitive in a range from about 1 mBar to about 100 Bar. In the case of a Pirani gauge, the choice of the value of the distance g separating both nanowires 2.1, 2.2 enables the pressure range accessible to the sensor to be determined.

Figure 5:
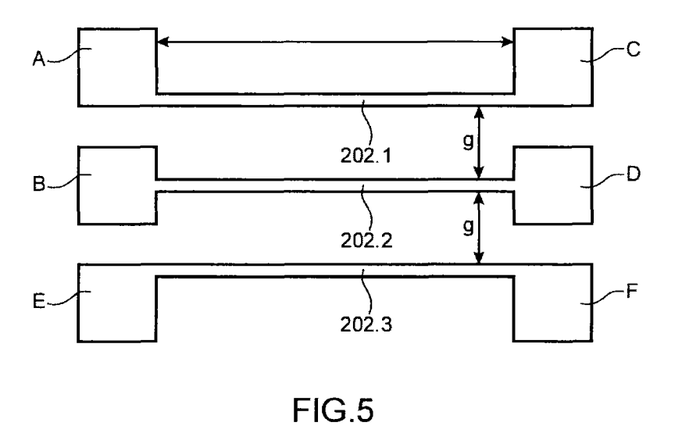
FIG. 5 is a schematic representation of an exemplary sensor with three nanowires.

In FIG. 5, another exemplary embodiment of a measuring device according to the present invention comprising three nanowires 201.1, 201.2, 201.3 suspended side by side on a support, being substantially in parallel to each other can be seen. Each nanowire is away from a directly neighbouring nanowire by a distance g. As a variant, it can be contemplated that the nanowires are not spaced apart by the same distance.

The anchoring points of each nanowire 202.1, 202.2, 202.3 are respectively designated A and C, B and D, E and F.

The nanowires can have an excitation function or a detection function.

In one example, the nanowire 202.2 located between the nanowires 202.1 and 202.3 is the excitation nanowire and the nanowires 202.1 and 202.3 form the detection nanowires. It is thereby possible to perform a differential measurement by applying the excitation signal on the centre nanowire 202.2 and combining the measurements obtained with each of the nanowires 202.1 and 202.3.

For the sake of simplicity, the biasing means and detection means connected to each of the nanowires are not represented.

In another example, the nanowires 202.1 and 202.3 form excitation nanowires and the nanowire 202.2 forms a detection nanowire. This device enables the amplitude of the temperature variations in the central nanowire 202.2 to be increased.

In another example, one of both end nanowires 202.1 or 202.3 is used as the excitation nanowire and the other end nanowire 202.3 or 202.1 and the centre nanowire are used as the detection nanowires.

Figure 6:
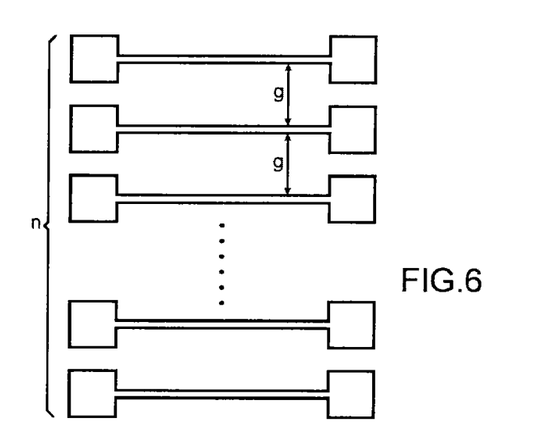
FIG. 6 is a schematic representation of an exemplary sensor with n nanowires.

In FIG. 6, another exemplary embodiment wherein the device comprises n nanowires disposed parallel to each other and away two by two by a distance g, n being a positive integer strictly higher than 1 can be seen, the cases n=1, n=2 and n=3 have already been described above in connection with FIGS. 1 to 5.

Advantageously, the sensor is intended to be disposed in a channel such that the n nanowires are disposed in the width of the fluid channel.

In one advantageous example, the device comprises n simple nanowires placed side by side in a plane by alternating an excitation nanowire and a detection nanowire. The excitation nanowires are connected in parallel and the detection nanowires are connected in parallel, thereby a sensor the resolution of which is increased is obtained.

Then, a spatial noise averaging is carried out on a great number of samples, actually reducing the noise by a factor $\sqrt{n}$. Such an implementation also enables the exchange area between the excitation nanowires and the detection nanowires to be increased.

From the noise point of view and still considering the same current flowing in each of the nanowires, the paralleling of n resistances enables the Johnson and Flicker noises to be reduced by decreasing the resistance value while keeping the same useful signal.

The parallel connection can be achieved by cross-connections, made with at least two metallization levels.

Further very advantageously, such a measuring device can enable heat exchanges to be characterized in a medium, for example the temperature profile to be determined in the channel width.

Figure 7A:
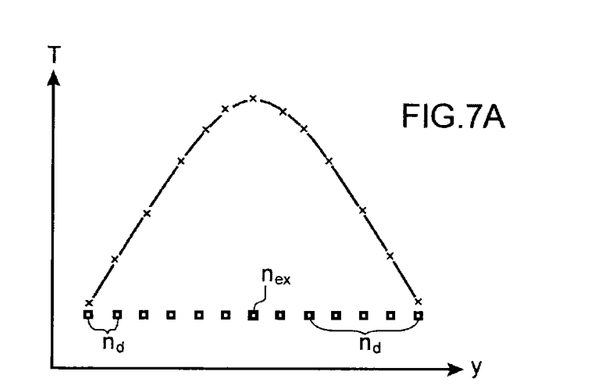
FIG. 7A is a schematic graphic representation of the temperature of different nanowires of a sensor according to the invention as a function of their position in a channel.
Figure 7B:
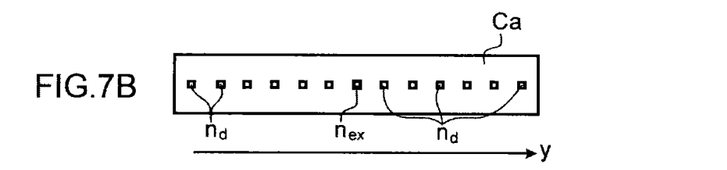
FIG. 7B is a transverse cross-section representation of a channel provided with a sensor with several nanowires according to the invention.

In FIG. 7A, the temperature T of each of the n nanowires is schematically represented as a function of its transverse position y in the channel Ca represented in FIG. 7B. The nanowire designated $n_{ex}$ located in the centre forms the excitation nanowire and the nanowires designated $n_d$ form detection nanowires. The transverse temperature profile of the inside of the channel Ca is thereby obtained.

This measurement enables heat transfers in the fluid channel to be characterized since it gives a piece of information about the heat exchanges by the gas.

Figure 8A:
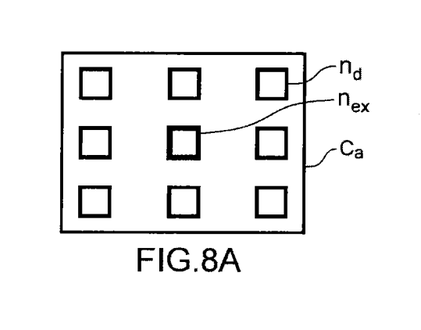
FIGS. 8A and 8B are schematic representations of sensors having several nanowires distributed in several layers.
Figure 8B:
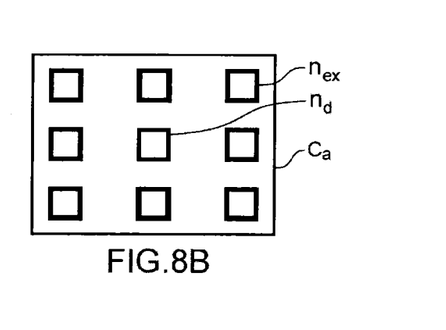

In FIGS. 8A and 8B, another exemplary embodiment of a measuring device, wherein the nanowires are distributed into parallel layers and thus distributed in several planes can be seen. The sensor thus extends in three dimensions.

The nanowires are distributed along the width and height of the channel. The channel Ca is represented in a transverse cross-section view. In this example, the channel has a rectangular cross-section.

For example, in FIG. 8A, the excitation nanowire is the centre nanowire designated $n_{ex}$, the other, nanowires $n_d$ being detection nanowires. This configuration enables heat exchanges along the width and height of the channel to be characterized.

In FIG. 8B, the peripheral nanowires $n_{ex}$ form the excitation nanowires and the centre nanowire $n_d$ forms the detection nanowire. Thus, the amplitude of the temperature variations in the centre nanowire $n_d$ are increased.

It will be understood that the arrangements of FIGS. 8A to 8B are presented by way of non-limiting examples and that other arrangements and/or number of excitation and detection nanowires are within the scope of the present invention. For example, the nanowires can be distributed as a crown around a centre nanowire, thus all the nanowires of the crown are equidistant from the centre nanowire.

In FIGS. 9A to 9D, exemplary embodiments of a thermal flow measuring device according to the present invention comprising one or more suspended elements of the first type, i.e. forming both the excitation and detection elements and thermostated masses, can be seen.

Figure 9A:
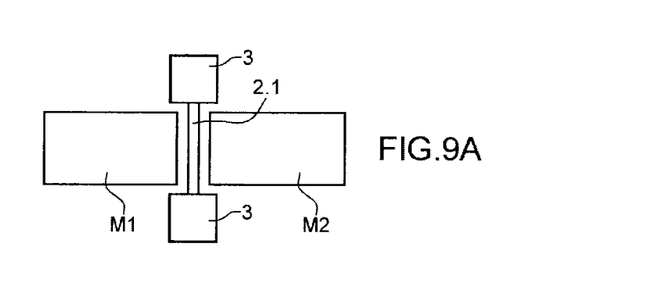
FIGS. 9A and 9B are top view and side view respectively of another exemplary measuring device implementing thermostated masses.

In FIG. 9A, a nanowire 2.1 surrounded by thermostated masses M1 and M2 located on either side of the wire can be seen. The thermostated masses are intended to improve removal of heat produced by the nanowire 2.1. For example, these masses are at the temperature of the support of the measuring device.

Figure 9B:
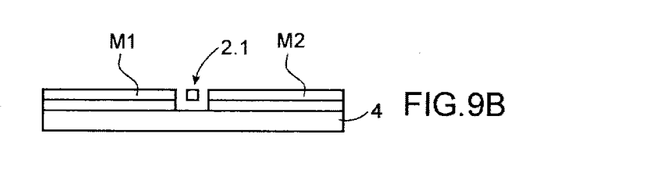

In FIG. 9B, a cross-section view of the device of FIG. 9A can be seen, in this example the thermostated masses are formed by silicon patterns at the temperature of the support, these patterns being made at the same time as the nanowire 2.1.

Figure 9C:
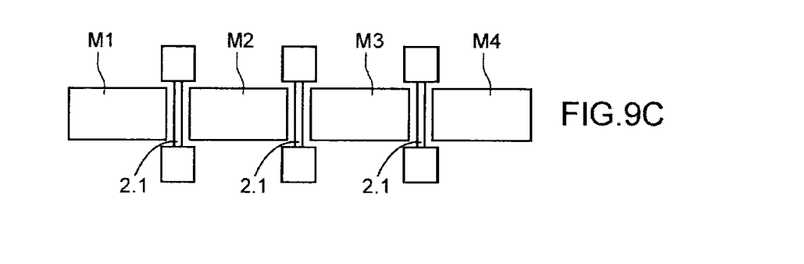
FIGS. 9C and 9D are top views of other exemplary embodiments of a measuring device implementing thermostated masses.

In FIG. 9C, an exemplary device can be seen, comprising n suspended elements of the first type only 2.1, and n+1 thermostated masses M1 to $M_{n+1}$ interposing between the nanowires such that each nanowire is surrounded by two masses. In the example represented, n is 3.

Each nanowire is linked to an alternating current source at the same frequency or a different frequency the intensity of which provides heating of the corresponding nanowire by Joule effect.

The implementation of the thermostated masses at the temperature of the support enables the exchange area between the thermostat formed by the support and the thermostated masses and the nanowire to be increased, and thus the exchanges with the gas to be increased which results in an improved sensitivity of the measuring device.

Figure 9D:
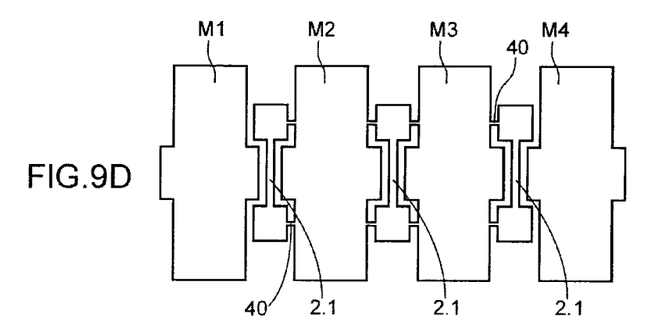

In FIG. 9D, the device comprises n suspended elements of the first type 2.1 and n+1 thermostated masses M1 to $M_{n+1}$ at the temperature of the support. The n elements of the first type are connected in parallel by connections 40 formed in a second metallization level. In the example represented, n is equal to 3. It will be understood that n can be any number.

An exemplary method for manufacturing a sensor according to the present invention will now be described.

In FIGS. 10A to 10H, schematic representations of different steps of the manufacturing method can be seen.

Figure 10A:
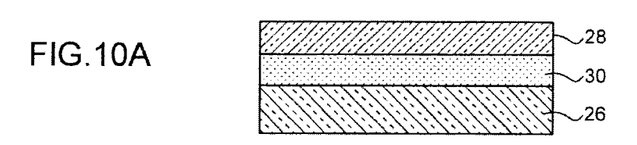
FIGS. 10A to 10H are schematic representations of different steps of an exemplary method for making a sensor according to the invention.

In the example described, a SOI (Silicon On Insulator) plate is used, represented in FIG. 10A. The SOI substrate comprises a silicon layer 26, a single crystal silicon layer 28, the layers 26, 28 being separated by a $SiO_2$ layer 30. The single crystal silicon layer 28 forms the front face.

Figure 10B:
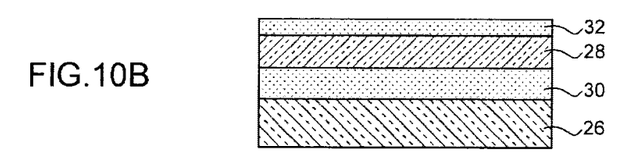

During a first step, a $SiO_2$ oxide layer 32 is deposited onto the layer 28. The resulting element is represented in FIG. 10B.

Figure 10C:
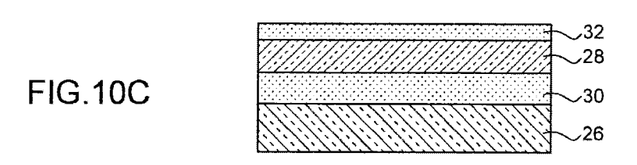

During a next step, a P++ doping, for example with boron, of the silicon layer 28 located between the oxide layer 30 and the oxide layer 32 is carried out.

The doping through the oxide layer enables a more even distribution of the dopants in the layer 28. The doping obtained is in the order of $1 \cdot 10^{19}$ at./cm$^3$). This doping has the effect of maximizing the temperature coefficient of resistivity of the silicon.

The resulting element is represented in FIG. 10C. The doping is symbolized by dots.

Figure 10D:
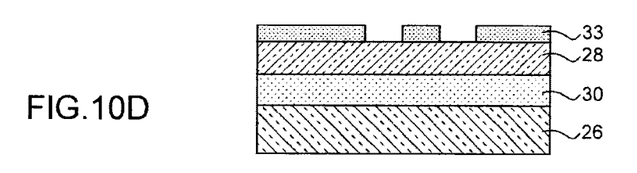

During a next step, the oxide layer 32 is removed and a resin layer 33 is deposited, wherein the outlines of the patterns are defined in the resin 32 by lithography, for example deep-UV (DUV) lithography or hybrid DUV and electron beam (e-beam) lithography. These lithography methods are well known to those skilled in the art and will not be described in further detail. The e-beam lithography allows to avoid effects related to light diffraction upon etching nanometer devices.

The resulting element is represented in FIG. 10D.

Figure 10E:
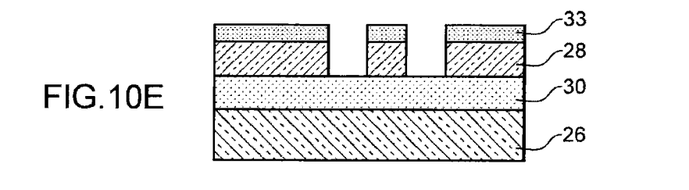

During a next step, the silicon layer is etched, for example by anisotropic RIE (Reactive Ion Etching).

The resulting element is represented in FIG. 10E.

Figure 10F:
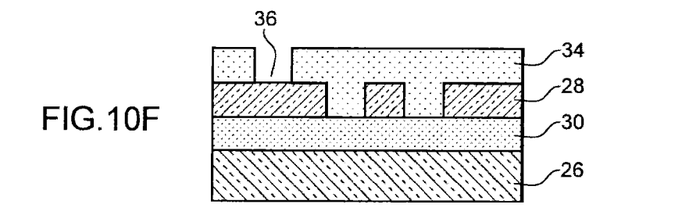

During a next step, a $SiO_2$ chemical deposition 34 is performed onto the etched silicon layer 28 which is then etched to bound the locations 36 of the electrical contacts, for example plasma etching.

The resulting element is represented in FIG. 10F.

Figure 10G:
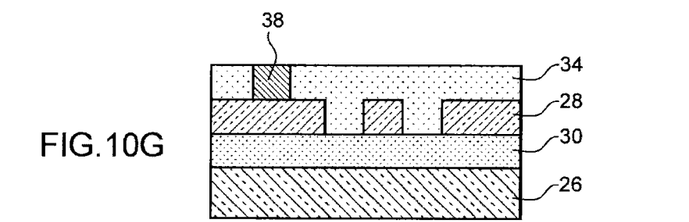

Then, the electrical contacts 38 are made by depositing for example aluminium, for example by spray deposition.

The resulting element is represented in FIG. 10G.

Figure 10H:
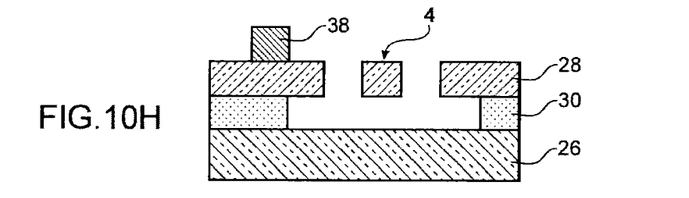

During a next step, the nanowire is released, for example by etching the layer 30, for example with vapour hydrofluoric acid.

The released structure is visible in FIG. 10H.

The thermal flow sensor according to the invention enables a gas concentration sensor or a Pirani sensor which is independent of the variation of the parameters of the external environment such as temperature variations to be made.

This sensor is particularly suitable for being associated to a gas chromatography micro-column. One or more sensors are disposed in a channel connected in series at the output of the micro-column and enable analyte peaks to be detected.

The invention claimed is:

1. A thermal flow sensor comprising:
   at least two elements suspended with respect to a support, said at least two suspended elements comprising n first suspended elements, n being a positive integer higher than 1, each first suspended element being of an electrically conductive material and each first suspended element comprising at least one nanowire, and m second suspended elements, m being a positive integer higher than 0, each second suspended element being of an electrically conductive material;
   first means for biasing each first suspended element comprising an alternating current source an intensity of which provides heating of each first suspended element by Joule effect;
   a first sensor for measuring variation amplitude of an electric voltage at terminals of each first suspended element;
   second means for biasing each second suspended element, comprising an alternating current source of a frequency different from that of the first biasing means or by a direct current source; and
   a second sensor for measuring variation amplitude of an electric voltage at terminals of each second suspended element, the variation amplitude of the electric voltage being based on a temperature variation of each second suspended element caused by the heating of each first suspended element.

2. The thermal flow sensor according to claim 1, wherein each second element is formed by at least one nanowire, substantially parallel to the first suspended element and away from the first suspended element by a given distance, and wherein the second sensor enables a quantity of heat transferred from a first suspended element to a second suspended element to be deduced.

3. The thermal flow sensor according to claim 1, wherein the n first suspended elements are provided substantially parallel to each other.

4. The thermal flow sensor according to claim 3, wherein the first suspended element is surrounded with m second suspended elements and/or the second suspended element is surrounded between n first suspended elements.

5. The thermal flow sensor according to claim 1, wherein the m second suspended elements are substantially parallel to each other.

6. The thermal flow sensor according to claim 5, wherein the n first suspended elements are provided substantially parallel to each other and wherein the first means for biasing the n first suspended elements, respectively the second means for biasing the m second suspended elements are common.

7. The thermal flow sensor according to claim 6, wherein the n first suspended elements and m second suspended elements are distributed in a plane or several parallel planes.

8. The thermal flow sensor according to claim 5, wherein the first suspended element is surrounded with m second suspended elements and/or the second suspended element is surrounded between n first suspended elements.

9. The thermal flow sensor according to claim 5, wherein the n first suspended elements are provided substantially parallel to each other and wherein the n first suspended elements and m second suspended elements are distributed in a plane or several parallel planes.

10. The thermal flow sensor according to claim 1, comprising at least two thermal masses linked to the support, the thermal masses being provided on either side of the first suspended element.

11. The thermal flow sensor according to claim 10, comprising n first suspended elements and n+1 thermal masses, n being higher than or equal to 2, said n+1 thermal masses being disposed such that each first element is surrounded by two masses.

12. The thermal flow sensor according to claim 1, wherein the first or second suspended elements have respectively a width between 10 nm and 1 µm, a length between 1 µm and 100 µm, a thickness between 10 nm and 1 µm.

13. The thermal flow sensor according to claim 1, wherein the n first suspended elements are provided substantially parallel to each other and wherein a distance separating two suspended elements is between 50 nm and 10 µm.

14. The thermal flow sensor according to claim 1, wherein the n first suspended elements are provided substantially parallel to each other and wherein a distance separating two suspended elements is between 50 nm and 10 µm.

15. The thermal flow sensor according to claim 2, wherein said thermal flow sensor comprising a first suspended element surrounded by m second suspended elements, is configured to be disposed in a channel, said suspended elements being disposed parallel to an axis of the channel so as to determine transverse heat exchanges in a gas inside the channel.

16. A system for determining the concentration of a gas environment comprising:
    at least one thermal flow sensor according to claim 1; and
    electronics for processing electric voltage values delivered by the thermal flow sensor.

17. A device for analysing a gas or gas mixture comprising:
    a gas chromatography column; and
    at least one system for determining the concentration according to claim 16, said determining system being disposed in a channel connected to an output of the gas chromatography column.

18. A system for determining pressure in a gas environment comprising:
    at least one thermal flow sensor according to claim 1; and
    electronics for processing electric voltage values delivered by the thermal flow sensor.

* * * * *